United States Patent [19]  
Beck et al.

[11] 4,252,653  
[45] Feb. 24, 1981

[54] HEMOPERFUSION DEVICE FOR SPECIFIC MODIFICATION OR REMOVAL OF COMPONENTS OF WHOLE BLOOD

[75] Inventors: Lee R. Beck, Birmingham, Ala.; Thomas A. Davis, Scotch Plains, N.J.

[73] Assignee: Stolle Research and Development Corporation, Cincinnati, Ohio

[21] Appl. No.: 936,886

[22] Filed: Aug. 25, 1978

[51] Int. Cl.³ .......................................... B01D 13/00
[52] U.S. Cl. .............................. 210/321.3; 210/927; 210/446; 210/507
[58] Field of Search ........... 210/321 R, 321 A, 321 B, 210/497.1, 493 M, 507, 247, 452, DIG. 23, 446; 195/DIG. 11, 66, 63

[56] References Cited  
U.S. PATENT DOCUMENTS

| 2,284,787 | 6/1942 | Winkler | 210/497.1 X |
| 3,390,779 | 7/1968 | Kumme et al. | 210/456 |
| 4,048,064 | 9/1977 | Clark | 210/24 X |
| 4,061,141 | 12/1977 | Hyden et al. | 128/214 |

OTHER PUBLICATIONS

Davis et al., Activated Carbon Fibers for Hemoperfusion, Trans. Amer. Soc. Arty. Int. Organs, 20-A, 1974, pp. 353-357.

Primary Examiner—Charles N. Hart  
Assistant Examiner—E. Rollins Cross

[57] ABSTRACT

A hemoperfusion device is disclosed for the specific modification or removal of components of whole blood. The device involves a 3-dimensional arrangement of fibers within a housing arranged to provide maximum exposed fiber surface and flow-channel diameter, while also reducing the tortuosity of the flow path. Desired effector molecules are bound to the fibers to allow them to contact the target components of the blood, whereby to remove the target components. Details of the fiber and effector molecules are disclosed and a specific device is described.

3 Claims, 2 Drawing Figures

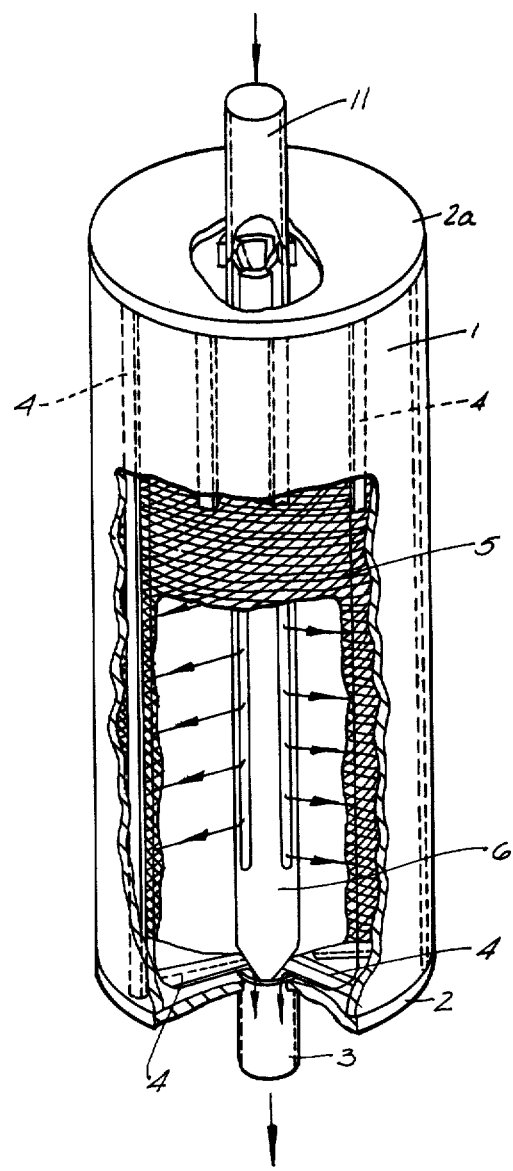

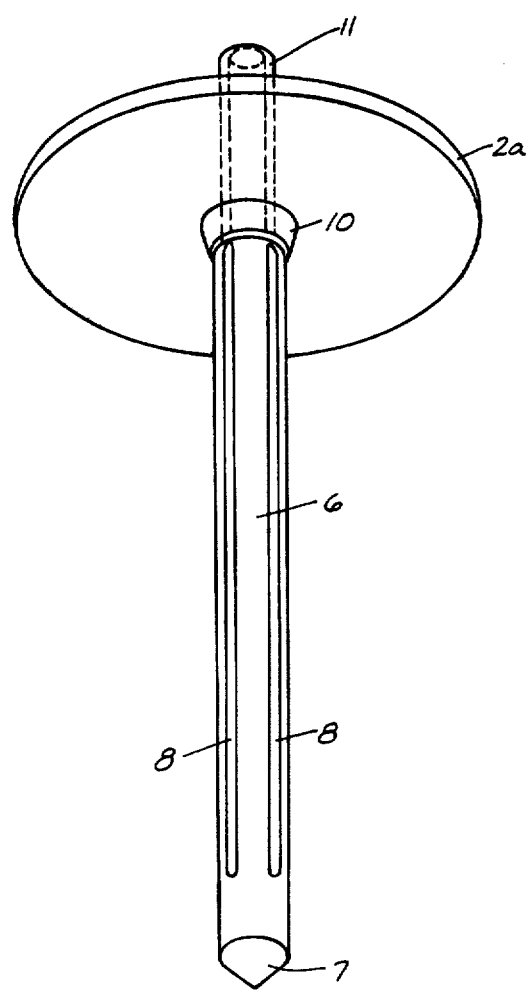

HEMOPERFUSION DEVICE FOR SPECIFIC MODIFICATION OR REMOVAL OF COMPONENTS OF WHOLE BLOOD

BACKGROUND OF THE INVENTION

The processes of blood filtration and hemoperfusion for purification of blood are well known. With few exceptions, the devices which are employed for these purposes are capable of removing substances only in a nonspecific manner. Removal of toxic or undesirable species from the blood is accomplished on the basis of molecular size, as by dialysis employing semipermeable membranes (see U.S. Pat. No. 3,619,423); on the basis of ionic nature, as by perfusion over ion-exchange resins (see U.S. Pat. Nos. 3,794,584; 4,031,010); or on the basis of affinity for adsorbents, as by perfusion over activated charcoal. These techniques exhibit severe limitations arising from lack of specificity. Within the fraction removed from the blood are hormones, nutrients, drugs, electrolytes, and other species, whose deletion from circulation may well result in adverse effects upon the perfused patient. Since patients requiring such treatment are suffering from drug overdose, renal or hepatic failure, or other conditions severely diminishing their vitality, further metabolic imbalance may be poorly tolerated. A further disadvantage of lack of specificity in hemoperfusion devices is the limited capacity for the target species. The target species must compete with other substances for the available binding sites on the adsorbent. Such devices must be inordinately large to ensure sufficient capacity for the target species.

In addition to the nonspecificity problems exhibited by these devices, further complications have arisen with respect to structure and flow properties. Damage to formed elements and macromolecular components of the blood, by hemolysis, platelet aggregation, fibrin formation, and leukocyte destruction, for example, are often observed when blood is exposed to nonbiological surfaces or to turbulent flow. Heparinizing patients is only partially effective in preventing such damage. Hemoperfusion devices incorporating randomly dispersed particulate adsorbents have shown a propensity to pack under flow conditions. The result is an excessive pressure drop and diminished flow across the device. Blood damage increases under such conditions.

Many attempts have been made to overcome these problems and to design devices that exhibit specificity and applicability and to a wider range of molecular species, in particular high-molecular-weight species. Some synthetic matrices which have been examined show specific affinity for particular solutes. One such device employs fluorocarbon plastics for the specific removal of endotoxin. (U.S. Pat. No. 3,959,128).

Further specificity has been achieved by the use of bioactive substances bound to inert organic or inorganic materials in hemoperfusion systems. Examples of this type are the following. The affinity of bilirubin and chenodeoxycholic acid for serum albumin has been exploited by several researchers. The antigen-antibody interaction has also been employed (Canadian Pat. No. 957,922). Immobilized antigens have been perfused with blood to remove antibodies to BSA, to DNA, to HSA and ovalbumin, to blood factor VIII, and to immunoglobulin fractions IgG and ImG. Immobilized antibodies (IgG IgM) have been employed in hemoperfusion systems to diminish circulating levels of drugs and endogenous species. Antibodies to digoxin, to DNA, to BSA, to tumor-associated antigens, and to donor-kidney antigens and multiple myeloma protein, and low-density lipoproteins have been immobilized in extracorporeal systems for a variety of therapeutic purposes.

Among the enzymes, cell extracts, and whole cells that have been immobilized in extracorporeal systems (Canadian Pat. No. 957,922) are urease, uricase, aspariginase, pancreatic cells, liver cells, and liver microsomes, nuclease, and catalase.

The properties of materials and devices brought into contact with circulating biological fluids have been extensively studied. Weetall et al. have listed the following criteria as a checklist in device design: "Some In Vivo and In Vitro studies of Biologically Active Molecules on Organic Matrixes for Potential Therapeutic Applications" in *Biomedical Applications of Immobilized Enzymes and Proteins*, T. M. S. Chang, Ed., Plenum Press, New York, N.Y. "(1) laminar flow, (2) velocity gradient should exceed 350/sec, (3) material in contact with blood should be relatively nonthrombogenic, (4) smooth surfaces should be maintained, (5) minimum flow channel diameter of about 100 μm, (6) avoidance of crushing or grinding action of support material." Two further criteria are of considerable importance: (1) maximum loading of active blood altering species per unit of priming volume, and (2) minimal resistance to active contact of said species with the blood component to be altered, i.e. contact should require a minimum of diffusion-controlled transport and the transport should be through minimally resistant matter.

To date all hemoperfusion systems employing highly specific detoxifying species isolated within the device have employed one of four arrangements: (1) isolation of the detoxifying species by partitioning it from the perfusing blood, employing semipermeable membranes (e.g. U.S. Pat. No. 3,619,423) or hollow-fiber tubes; (2) encapsulation in or attachment to particulate materials (e.g. U.S. Pat. No. 3,865,726); (3) attachment of the species to a nonporous membrane or other planar surface (e.g. U.S. Pat. No. 3,959,128); or (4) attachment to the internal surface of polymeric tubes through which blood is passed (e.g. Canadian Pat. No. 957,922).

None of these systems meets all of the criteria listed above. Semipermeable membrane and hollow-fiber devices impose strong diffusion requirements for active participation of isolated elements and are limited to activity with low-molecular-weight species in the blood. Devices employing particulate components in which the active species is microencapsulated or sequestered within the pores of the support suffer from the same limitations of diffusion resistance, and additionally exhibit flow resistance due to packing, as well as blood damage arising from the grinding action of particulate movement. Nonporous planar surfaces and polymeric tubes have low surface area and thus insufficient capacity for active elements.

An alternative to these arrangements is the use of fiber-filled cartridges. Fibers have long been employed in blood contacting devices for removing aggregates of blood components during transfusion (e.g. U.S. Pat. No. 3,462,361). Polymeric fibers having pyrolytic carbon deposited on their surface and deployed in a random mass have been employed as nonspecific adsorbants in hemoperfusion (e.g. U.S. Pat. No. 3,972,818). Antibodies and other proteins have been incorporated into cellulose fibers by entrapment, for application in radioimmunoassay and for industrial use (e.g. U.S. Pat. No.

4,031,201). Antigens have been attached to nylon catheters and inserted into arteries for the removal of antibodies from the circulation.

In the art of hemoperfusion, devices designed for highly specific alteration of blood composition and containing fibers have been employed with limited success. Hersh and Weetall (supra) used a cartridge containing bio-active molecules bound to randomly dispersed, nonporous, polyester fibers. Both enzymes and antibodies have been immobilized by their technique. These devices represent a significant improvement over previous hemoperfusion systems with respect to minimizing damage to formed elements of the blood. Some problems with this design still remain however. Unanchored, randomly dispersed fibers tend to pack under the desired flow rates when sufficient fiber is available to furnish the requisite amounts of the bound active species. Furthermore, channeling (uneven distribution of flow) which is inevitable with this fiber arrangement results in diminished efficiency for the device.

Antibodies attached in a rigidly fixed 2-dimensional array have been described and employed for the removal of whole cells from blood in vitro (e.g. U.S. Pat. No. 3,843,324). This system, however, would not be applicable to hemoperfusion.

Polymeric fibers having carbon particles encapsulated within the polymer and being deployed in a nonrandom fashion within a hemoperfusion cartridge have been described by Davis et al. (Trans. Amer. Soc. Artif. Int. Org. 20:353). Although limited to application in nonspecific adsorption, this device exhibited superior properties with respect to capacity, cost, flow properties, and diminished damage to the perfusing blood.

BRIEF SUMMARY OF THE INVENTION

According to the present invention the problems discussed herein are avoided by a 3-dimensional arrangement of fibers to maximize the exposed fiber surface and the flow-channel diameter and to reduce the tortuosity of the flow path.

The hemoperfusion device of the present invention exhibits many features of the device described by Davis but has been extended and modified to allow its application to highly specific alteration to biological fluid composition. The fiber cartridge employs a fixed, nonrandom, three-dimensional array of fibers whose chemical composition is such that additional chemical species may be grafted onto the surface or encapsulated within the matrix of the fibers. The additional species are fixed in such manner that they may efficiently effect highly specific alterations upon biological fluids perfused through said cartridge. It is a further purpose of this invention to disclose generalized formulations and processes by which said cartridge may be manufactured. Lastly it is the purpose of this invention to disclose applications of said cartridge to effect the removal, collection, degradation, or modification of chemical species contained in biological fluids perfused through said cartridge.

BRIEF DESCRIPTION OF THE FIGURES OF THE DRAWING

FIG. 1 is a cutaway perspective view of an assembled hemoperfusion cartridge.

FIG. 2 is a perspective view of the spindle for the cartridge.

DETAILED DESCRIPTION

The present invention consists generally of a fixed 3-dimensional array of fibers contained within a housing, which provides for a continuous flow of fluid through the housing with maximum contact between fluid and fibers. Further it is a property of this device that specific bioactive effector molecules can be bound to the fibers thus to allow the effector molecules to contact target components of the fluid and thus alter the composition of the fluid.

Fibers—Necessary Properties, and Suitable Categories

The art of attaching biologically active molecules to insoluble materials is well known. The specific insoluble materials applicable to the present invention are defined by several criteria: (1) the material must be able to be formed into fibers strong enough for processing into a three-dimensional array; (2) the fibers must be essentially insoluble under neutral aqueous conditions; (3) the fibers should possess a smooth nonporous surface to reduce blood damage and decrease nonspecific adsorption; (4) the fibers must release no toxic substances or fragments into the aqueous media percolating through them; (5) the degree of biocompatibility of the fiber composition should be commensurate with the intended application. For long-term or chronic applications in hemoperfusion, the fiber must cause no irreversible cumulative deleterious alterations of the quantity or vital capacity of circulating species. In short-term or emergency applications, the fibers need only permit efficient passage of heparinized or otherwise anticoagulated blood without the occurrence of thrombosis or hemolysis beyond the limits of the patient's vital capacity. (6) The fibers employed must exhibit properties which will allow the nonreversible attachment or englobement of the active species. The preferred fibers would be those shown to be substantially compatible for implantation within the body. Such fibers may be chosen from one of the following categories: (1) substances of biological origin or products arising from them, i.e., cellulose, perfluoroethyl cellulose, cellulose triacetate, cellulose acetate, nitrocellulose, dextran, chitin, collagen, fibrin, elastin, keratin, crosslinked soluble proteins, polymerized soluble organic species of biological origin (polylactic acid, polylysine, nucleic acids), silk, rubber, starch, and hydroxyethyl starch; (2) heterochain synthetic polymers, such as polyamides, polyesters, polyethers, polyurethanes, polycarbonates, and silicones; (3) hydrocarbon polymers such as polyethylene, polypropylene, polyisoprenes, polystyrenes, polyacrylics such as polyacrylamide, polymethacrylate, vinyl polymers such a polyvinylacetate, and halogenated hydrocarbon plastics such as polyvinylcholoride, polyfluorocarbons like Teflon, fluorocarbon copolymers and polychlorotrifluoroethylene; (4) inorganic fibers such as fiberglass.

The above examples of polymers vary widely in their blood compatibility. Several techniques have been described, however, which modify the blood compatibility of otherwise unacceptable materials, among these are coating the materials with more compatible substances (e.g. U.S. Pat. No. 4,073,723) or with antithrombogenic substances such as heparin.

Fiber Configuration and Housing

Fiber dimension and the specific 3-dimensional array of fibers within the cartridge will determine the flow properties, available polymer surface area, and priming volume exhibited by the device. The last two conditions will be optimized when the fiber diameter is at the minimum value yielding sufficient strength and when the fiber array is chosen to yield a maximally compact bed. The flow properties will be affected in the opposite manner to that of available surface area and priming volume. These conditions must then be adjusted in order to optimize the overall efficiency with minimal blood damage.

The deployment of the fixed fiber array between the inlet and outlet of the cartridge jacket may be chosen from innumerable configurations. Among the more convenient configurations are the following. (1) Deployment of fibers by winding about the outlet or inlet port. Such configurations may possess cylindrical symmetry about a tubular port having means for influx or efflux of fluid along the length of the tube. In another possible configuration of wound fibers, the fibers may be wound with spherical symmetry about a single central port. (2) In cartridges wherein the fluid flows axially through the cartridge, the fibers may be deployed parallel to the direction of flow, being attached at each end of the cartridge. Another configuration employing an axial flow cartridge may have the fibers deployed transversely to the flow of blood by attachment of the fibers to the lateral portions of the cartridge. A combination of parallel and transverse configuration may also be employed in which the fibers may be attached at both the ends and the lateral portions of the cartridge thus deployed in an interwoven fashion.

Fibers may be deployed as monofilaments or as multifilament yarns, and the device may contain one continuous fiber or numerous fibers. It is required only that the configuration of the cartridge housing and fiber deployment be consistent with fluid dynamics, compatible with minimal damage to the formed fluid components perfused through the device. These restrictions are well known to those skilled in the art.

Effector Molecules

The highly specific effector molecules having activity toward biological fluid components of endogenous or exogenous origin, and being attached to the fibers within the device, may be selected from one or more of the following species. The molecules may be all or a fragment of an antibody, antigen, allergin, complement factor, clotting factor, enzyme, substrate of an enzyme, cell surface receptor molecule, vaccine, enzyme inhibitor, hormone, tissue homogenate, purified protein, toxin, nucleic acid, polysaccharide, lipid, intact cell, microcapsule, liposome, polymer, antibiotic, chemotherapeutic agent, therapeutic drug, organic species having high affinity for a specific biological fluid component, or an inorganic species having high affinity for specific biological fluid component.

Means of Attachment of Effector Molecule to Fiber

The chosen effector molecule may be bound to the device by means well known to those skilled in the art, particularly for immobilized enzymes (e.g. U.S. Pat. No. 4,031,201), affinity chromatography (e.g. U.S. Pat. No. 3,652,761), solid phase immunoassay (e.g. U.S. Pat. No. 4,059,685), bonded stationary phase chromatography hemoperfusion (e.g. U.S. Pat. No. 3,865,726), enzyme-linked immune-sorbant assay, cell labeling and separating, and hemodialysis (e.g. Canadian Pat. No. 957,922).

Attachment of the effector molecule to the fibers may be performed during polymer preparation, fiber spinning, just prior to placement of said fibers into the cartridge, or following the deployment of the fibers in the cartridge.

Cartridges may be stored dry after lyophilization or filled with a buffer containing antimicrobial agents. Sterilization of the device may be performed prior to the incorporation of the active species onto the fibers with all subsequent steps performed with sterile reagents, or sterilization may be performed following the incorporation.

The Cartridge

The assembled cartridge is composed of a glass or plastic jacket 1, capped at one end by a circular glass or plastic disk 2, and at its other end by a similar disk 2a. The disk 2 has at its center a cylindrical exit port 3. The jacket and cap have raised elements in the form of ribs 4 allowing for the unhindered axial flow of fluid along the suface of the jacket and cap, and allowing the exit thereof via the port. Within the jacket is a spool of fiber 5, helically wound about a glass or plastic spindle 6. The spindle and fiber fill the entire volume of the jacket with the exception of the space between ribs.

FIG. 2 shows the spindle 6 which is a glass or plastic rod which is conical at its base 7 and is slotted along its length as at 8. The rod is fitted at its top into a conical port 10, which is attached to the circular spindle cap of like composition 2a. The diameter of the cap is chosen so that it makes a tight fit with the jacket and forms a sealed vessel when the spindle is inserted into the jacket. The external surface of the spindle cap has affixed to it a cylindrical entrance port 11 which is opposed to the conical port 10 and has an internal diameter which allows access of fluid passing through it to the slots 8 of the spindle 6. Furthermore, the conical bases of the spindle is of dimensions such that placement of the spindle base into the exit port results in contact of the spindle only with the ribs 4 of the jacket cap. This allows the fluids which accumulate between the ribs to exit through the lumen between the conical base 7 of the spindle 6 and the exit port 3. Thus, when the spindle is wound with a fiber, the flux of fluids entering through the device is that denoted by the arrows in FIG. 1.

The fiber wound about the spindle is a monofilament having a diameter in the range 0.05 to 2.0 mm. It is composed of hydroxyethyl cellulose (HEC). Following the incorporation of the wound spindle into the housing, the device is sealed and filled with dioxane containing 20% of hexamethylenediisocyanate. The fibers are allowed to stand for 48 hours at room temperature and are then washed with distilled water. This operation generates a fiber coil exhibiting covalently bound primary amines on its surface. The distilled water is then replaced by an aqueous solution containing 0.25% of IgG and 1% of water-soluble carbodimide, pH 5.5. The IgG may have been acylated to eliminate endogenous primary amines. Following 24 hours of exposure to this solution, the device is washed exhaustively with distilled water and sterilized for use in in vivo perfusion applications.

Modifications may be made in details of the invention and therefore no limitation which is not specifically set forth in the claims is intended and no such limitation should be implied.

What we claim is:

1. A hemoperfusion device comprising an elongated housing of impermeable material, closed at its ends by means of impermeable end plates, said housing on its interior having a plurality of axial ribs extending substantially throughout the length thereof, an inlet port in one of said end plates, an outlet port in the other of said end plates, said ribs continuing radially in said other of said end plates, an impermeable spindle axially disposed in said housing and having axially disposes grooves in its periphery, a conical port secured to one end of said spindle and in communication with said inlet port and with said grooves, said spindle at its other end terminating in a conical tip axially disposed with respect to said outlet port with an annular space therebetween, and a spool of fiber helically wound on said spindle to substantially fill the interior of said housing to said ribs, whereby blood entering said inlet port flows along said spindle grooves, passes through said fiber spool, flows along the inside of said housing between said ribs, and thence between said conical tip and said outlet port, said fiber having attached thereon specific effector molecules having activity to remove biological fluid components of endogenous or exogenous origin from blood being perfused through said device.

2. The hemoperfusion device of claim 1 wherein said fiber is a monofilament having a diameter between about 0.05 mm and about 2.0 mm, on which effector molecules can be immobilized in such manner that they are free to react chemically with factors in the blood, thereby removing such factors from the blood.

3. The hemoperfusion device of claim 2 wherein said fiber is of hydroxyethyl cellulose.

* * * * *